United States Patent [19]

Chu

[11] Patent Number: 4,675,188

[45] Date of Patent: Jun. 23, 1987

[54] GRANULAR ANHYDROUS DICALCIUM PHOSPHATE COMPOSITIONS SUITABLE FOR DIRECT COMPRESSION TABLETING

[75] Inventor: Chihang R. Chu, Yonkers, N.Y.

[73] Assignee: Stauffer Chemical Company, Westport, Conn.

[21] Appl. No.: 761,986

[22] Filed: Aug. 2, 1985

[51] Int. Cl.$^4$ .................. C01B 15/16; C01B 25/26; A61K 33/06; A61K 7/16

[52] U.S. Cl. ........................... 424/154; 424/57; 424/128; 424/465; 423/307; 423/308; 514/835; 514/778; 514/780

[58] Field of Search .............. 424/14, 57, 154, 128; 423/307, 308; 514/835, 778, 780

[56] References Cited

U.S. PATENT DOCUMENTS

| | | | |
|---|---|---|---|
| Re. 29,077 | 12/1976 | Geller | 424/15 |
| 2,018,410 | 10/1935 | McDonald et al. | 424/57 |
| 2,196,150 | 4/1940 | Heald | 424/57 |
| 2,943,982 | 7/1960 | Dahlin | 424/57 |
| 3,068,067 | 12/1962 | Aia | 423/308 |
| 3,095,269 | 6/1963 | Chiola et al. | 423/308 |
| 3,134,719 | 5/1964 | Sheth et al. | 167/82 |
| 3,208,821 | 9/1965 | Lehr et al. | 23/109 |
| 3,210,154 | 10/1965 | Klein et al. | 23/106 |
| 3,334,979 | 8/1967 | Saunders et al. | 423/313 |
| 3,353,908 | 11/1967 | Cremer et al. | 423/159 |
| 3,784,708 | 1/1974 | Ranucci et al. | 424/357 |
| 3,829,562 | 8/1974 | Kim et al. | 424/57 |
| 4,036,928 | 7/1977 | Valenta | 264/115 |
| 4,044,105 | 8/1977 | Enomoto et al. | 423/308 |
| 4,048,337 | 9/1977 | Fabbian | 424/357 |
| 4,115,307 | 9/1978 | McGilvery | 252/135 |
| 4,154,799 | 5/1979 | Hauge | 423/308 |
| 4,187,803 | 2/1980 | Valenta | 119/1 |
| 4,193,973 | 3/1980 | Jarvis et al. | 423/308 |
| 4,244,931 | 1/1981 | Jarvis et al. | 423/308 |
| 4,247,526 | 1/1981 | Jarvis et al. | 423/308 |
| 4,472,365 | 9/1984 | Michel | 423/308 |
| 4,487,749 | 12/1984 | Sherif et al. | 423/308 |
| 4,496,527 | 1/1985 | Sherif et al. | 423/308 |
| 4,524,054 | 6/1985 | George et al. | 423/308 |

FOREIGN PATENT DOCUMENTS

| | | | |
|---|---|---|---|
| 59-223206 | 12/1984 | Japan | 424/57 |
| 59-223208 | 12/1984 | Japan | 424/57 |
| WO81/02521 | 9/1981 | PCT Int'l Appl. | |

OTHER PUBLICATIONS

John R. Van Wazer, *Phosphorus and its Compounds*, vol. 1: Chemistry, Interscience Publishers, Inc., New York, N.Y., 1958, pp. 521, 522, 1646 and 1651.
Kirk–Othmer Encyclopedia of Chem. Tech., 3rd Ed. vol. 17, p. 446 (also page 445).
Chem. Abstracts 94, 90250z (1981).
Chem. Abstracts 95:12650m (1981).
Chem. Abstracts 95:67921f (1981).
Chem. Abstracts 79:111315g (1973).
Chem. Abstracts 92:203506s.

*Primary Examiner*—Ronald W. Griffin
*Attorney, Agent, or Firm*—Paul J. Juettner

[57] ABSTRACT

A granular directly compressible anhydrous dicalcium phosphate having a particle size sufficient for efficient direct compression tableting, preferably at least 90 percent greater than 44 microns, a dentin abrasion value of less than 150 and a surface area of greater than 5 meters$^2$/gram can be prepared by dehydrating particles of soft dicalcium phosphate dihydrate of a particle size insufficient for direct compression tableting, preferably at least 10 percent less than about 44 microns such as by heating at a temperature sufficient to form anhydrous dicalcium phosphate. The dehydrated particles are then granulated with a binder. The product is a granular anhydrous dicalcium phosphate exhibiting good compressibility and flowability while being in an anhydrous state.

12 Claims, No Drawings

GRANULAR ANHYDROUS DICALCIUM PHOSPHATE COMPOSITIONS SUITABLE FOR DIRECT COMPRESSION TABLETING

The present invention relates to granular anhydrous dicalcium phosphate compositions which are suitable for direct compression tableting and to tablets produced by direct compression.

BACKGROUND OF THE INVENTION

In compressing a dry particulate material into tablets, the direct compression technique is the most desirable. It employs the fewest steps and, in the case of pharmaceutical tablets containing sensitive or unstable active materials, minimizes the contact of the active ingredient with water, organic solvents or other conditions tending to adversely effect the stability thereof.

Tableting material for dry direct compression must be compression into a tablet form, and must produce strong tablets with good tablet surfaces and good strength, particularly under the stress of automatic tableting equipment. The direct compression vehicle must be flowable into the dies of high speed tableting machines without bridging as so often occurs with fine powders. Since the amount of active material contained in a tablet is based on the weight of the tablet, weight variations caused by improper flow cannot be tolerated. The vehicle must also have good stability under normal ambient conditions so that it can be effectively compressed.

Most powdered dry materials are impractical for direct compression tableting, particularly in automatic tableting equipment, due to lack of flow. Some of these powders can be granulated using a wet granulation process, with or without the addition of an adhesive substance. The moistened powder is converted into a crumbly mass which is forced through a screen to reduce the material to a grain-like structure of small granules. It is then dried, milled and sieved.

The powder can also be dry granulated by precompressing the dry powder, such as, into slugs or passing the material between two compressing rollers followed by breaking the material into granular particles of uniform size.

Granular tricalcium phosphate, also known as granular tribasic calcium phosphate, and unmilled dicalcium phosphate dihydrate, also known as unmilled dibasic calcium phosphate dihydrate, are effective direct compression vehicles.

Anhydrous dicalcium phosphate, which has also be used in tableting, has generally been prepared by precipitating the product from a slurry of lime and phosphoric acid which has been heated above 80° C. (see U.S. Pat. No. 3,095,269). U.S. Pat. No. 3,334,979 discloses a precipitated anhydrous dicalcium phosphate which is a hard abrasive material having a dentin abrasion value (Radioactive Dentin Abrasivity) of about 200 (see discussion of Radioactive Dentin Abrasivity on page 7). Precipitated anhydrous dicalcium phosphate is a fine, dense powder which must be agglomerated with a binder such as starch before it can be used in direct compression tableting.

Anhydrous dicalcium phosphate can also be prepared by driving off the water of hydration at moderately elevated temperature in the presence of free moisture, though a hard mass is often obtained (Kirk-Othmer, Encyclopedia of Chemical Technology, 3rd Edition, Vol. 17, page 446). U.S. Pat. No. 3,095,269 discloses the preparation of anhydrous dicalcium phosphate by boiling a slurry of DCPD at a pH below 5.5. At pH's near 5.5, cubic crystals of a size smaller than the diamond shaped crystals achieved at lower pH's are obtained. U.S. Pat. No. 3,095,269 further teaches that there is a problem in controlling the drying rate to effect gradual release of large quantities of chemically bound water. Excessive rate of drying tends to cause degradation of well-formed crystals due to sudden release of the water. This results in excessive break-up or fracture of the dihydrate particles, formation of fines and wide particle size distribution. U.S. Pat. No. 3,334,979 discloses that the dentin abrasion value of a dehydrated dicalcium orthophosphate dihydrate is about 60 (see discussion of Radioactive Dentin Abrasivity on page 7).

Anhydrous dicalcium phosphate can also be prepared by precipitation from a mother liquor containing a combination of monoammonium phosphate with ammonium and calcium chloride (U.S. Pat. No. 3,068,067). Anhydrous dicalcium phosphate can also be prepared from a monoalkali metal phosphate solution in combination with gypsum in a mill (U.S. Pat. No. 3,353,908).

These anhydrous dicalcium phosphates alone cannot be used in dry direct compression as the particles are too fine and will not flow into the compression dies. Some of these compounds cannot meet U.S. Pharmacopia (U.S.P.) standards without further treatment as they contain ammonium, chloride or sulfate ions. Some of these anhydrous compositions cannot be dry granulated to make a dry direct compression tableting composition.

SUMMARY OF THE INVENTION

In accordance with the present invention there is provided a new soft agglomerated anhydrous dicalcium phosphate which can be direct compression tableted characterized by granules of a particle size sufficient for direct compression tableting, a dentin abrasion value of less than 150 and a surface area prior to agglomeration greater than 5 meters$^2$/gram. The product is a "soft" granular anhydrous dicalcium phosphate which is a direct compression vehicle exhibiting good compressibility and flowability while being in an anhydrous state.

This new product can be prepared by dehydrating dicalcium phosphate dihydrate powder having sufficient fine particles that prevent effective direct compression tableting, preferably wherein at least 10 percent of the particle size is less than about 44 microns by heating at a temperature sufficient to produce anhydrous dicalcium phosphate. Preferably, dehydration is conducted by heating at a temperature and for a time sufficient to reduce the Loss on Ignition (L.O.I.) at 800° C. to an amount ranging from about 11 percent to about 6.6 percent by weight.

The thermally dehydrated dicalcium phosphate powder is then agglomerated and granulated with a binder to provide a granular "soft" anhydrous dicalcium phosphate which is flowable and directly compressible. It has unexpectedly been found that the product of the invention provides a surprising increase in compressibility even at low pressures. The product of the invention can be compressed into tablets which provide improved strength at lower tableting pressures without substantial loss in disintegration properties as compared to tablets prepared using granulated precipitated anhydrous dicalcium phosphate. Tablet weight variations within acceptable limits are provided.

DETAILED DESCRIPTION OF THE INVENTION

The invention utilizes powdered dicalcium phosphate dihydrate which can be prepared by any known process which prepares soft anhydrous dicalcium phosphate as defined herein. By powdered it is intended to mean a product containing a sufficient amount of fines which prevent the formation of tablets efficiently by direct compression. Preferably, powdered is intended to mean that at least 10 percent of the particles are less than 44 microns (through 325 mesh—U.S. Standard Sieve Series). More preferably, at least 20 percent and most preferably 30 percent is less than 44 microns. The particles are sufficiently small so as to allow granulation without forming substantial amounts of particles too large to be used in tableting. Preferably, the particles are less than 5 percent greater than 250 microns (on 60 mesh) and more preferably less than 20 percent greater than 149 microns (on 100 mesh).

The powdered dicalcium phosphate dihydrate (normal L.O.I. of about 25 percent) which can be prepared by any method known to those of ordinary skill in the art is dehydrated by heating to a temperature and for a time sufficient to reduce the L.O.I. below about 11 percent. Preferably, the L.O.I. is reduced to a range of from about 6.6 percent to about 8.5 percent, the range given in U.S. Pharmacopia for anhydrous dicalcium phosphate. 6.6 percent is the calculated lower L.O.I. limit for anhydrous dicalcium phosphate. Any further weight loss below the L.O.I. of 6.6 percent occurs by formation of pyrophosphate.

Dehydration can be initiated at about 75° C. Temperatures of above about 90° C. are preferred for higher rates of dehydration. Temperatures above 300° C. are not desirable as they may lead to pyrophosphate formation. The type of equipment may contribute to the temperature range utilized. Heating times can vary depending on the temperature and equipment used. These conditions are easily determined by one of ordinary skill in the art.

The porous anhydrous dicalcium phosphate can also be prepared by boiling a dicalcium phosphate dihydrate. Boiling can be conducting at pH's ranging from neutral to about 3. Dehydration will cause a drop in pH of from 1 to 2 pH units. The pH can be neutralized after anhydrous formation with a base, calcium bases such as lime being preferred.

The dehydrated soft anhydrous dicalcium phosphate is then granulated into granules having a particle size at least 90 percent above 44 microns or granules which can be comminuted into the desired particle size range. Binders and processes which are presently used to agglomerate precipitated anhydrous dicalcium phosphate can be used to agglomerate the soft powdered anhydrous dicalcium phosphate. The granulation can be conducted with any known binder such as starches, modified or unmodified; gums such as acacia, locust bean, guar and the like; synthetic polymer binders such as polyvinylpyrrolidone; cellulose derivatives such as cellulose ethers including, for example, hydroxypropyl methylcellulose, hydroxypropyl cellulose; gelatins such as gelatin and gelatin hydrolysates; and the like. The end use of the excipient can dictate type, quality and purity of the binders.

The starch can be any starch or blends thereof, modified or unmodified, which is soluble (swellable) under the conditions of use. The starch can be derived from cereal grains, i.e., corn, sorghum, rice and preferably wheat; tubers or roots such as cassava (tapioca), potato or arrowroot and the pith from sago palm. The starch can be unmodified and not treated to reduce viscosity (thin boiling) or pregelatinized to improve the cold water solubility.

The amounts of binders used can vary depending on the binding capacity and viscosity of the binding solution. For example, starch solutions may require less binder than less viscous acacia gum solutions. The ability of a binder to flow within the porous surface of the anhydrous dicalcium phosphate can be a function of viscosity. Optimum amounts of binder can be determined without undue experimentation by one of ordinary skill in the art. Amounts of binder can range from about 2 percent to about 10 percent based on the weight of the anhydrous dicalcium phosphate.

Granulation processes using binders include such known techniques as fluid bed granulation and wet granulation (blending followed by extrusion). Granulating procedures which rely on compacting as well as severe grinding are to be avoided as the particle structure developed by dehydration can be seriously affected.

The agglomerated product can be then classified by any means appropriate to produce the particle sizes which can effectively be used in direct compression tableting. While not desirable, mild grinding can be used to reduce the size of large granules, preferably isolated prior to grinding.

The product is classified to provide the desirable particle size for a direct compression vehicle. Any appropriate screening or sieving device including screens, perforated plates, cloth and the like, and air separators and the like can be used if appropriate classification of particles can be obtained.

The agglomerated anhydrous dicalcium phosphate particles of the invention preferably have granules of at least 90 percent above 44 microns (325 mesh), and preferably at least 80 percent above 74 microns (200 mesh). The upper limit on particle size is that size which can be processed in a tableting machine. Preferably, particle size is less than about 840 microns (20 mesh) and more preferably less than 50 percent greater than 420 microns (40 mesh) for flowability into the tableting machine. The lower limit on particle size is greater than that which is flowable into the tableting machine.

Following classification, the particles having the desired particle size range are segregated for further processing. The fine and large particles can be recycled for further processing.

Fines of smaller than 44 microns can be included in the product if not excessive, i.e. does not prevent proper flow into the direct compression dies (less than about 10 percent), or separated by particle classification means such as those discussed above.

The product of the invention is an anhydrous dicalcium phosphate which can be characterized in "soft" in its abrasiveness. By "soft" is meant having a "dentin abrasion value" or Radioactive Dentin Abrasivity (RDA) values of below 150 and preferably below 100. The abrasiveness of the anhydrous dicalcium phosphate was determined by the procedures set forth in the Journal of Dental Research, Volume 55, Number 4, 1976, p. 563; wherein "dentin abrasion values" are assigned after a dentifrice composition has been utilized in the mechanical brushing of radioactive dentin from extracted human teeth. The roots of previously extracted teeth are made radioactive and are brushed for a standard number of strokes at a standard pressure using a slurry containing the abrasive material. The radioactive phosphorus 32 removed from the dentin is used as an index of abrasion. A standard using calcium pyrophosphate is arbitrarily assigned a value of 100. The dentin abrasion values presently used are one-fifth that of the values in the original test. The standard calcium pyrophosphate, which was originally assigned an arbitrary abrasion value of 500, has been reassigned a value of 100. As used herein, all dentin abrasion values, even those in reference material, have been normalized to the later standard.

The surface area of the anhydrous product is greater than about 5 meters$^2$/gram and preferably greater than 7 and more preferably greater than 9 meters$^2$/gram as determined by the BET nitrogen absorption method. The upper limit of surface area is dictated by practical considerations of product manufacture.

The products of the invention can be made into tablets by direct compression using well-known techniques. Prior to tableting, the active ingredient(s) along with other ingredients such as binders, disintegrants, colorants, flavors, diluents and any other materials normally used in tablets can be blended with the granules. A lubricant is usually blended last to coat the surface of the particles and provide exterior lubrication.

After mixing, the blend can be formed into a tablet by dry, direct compression. Either single hydraulic units or multiple anvil high-speed rotary tableting units can be used as known in the industry. The tablets can be formed in the shape of round tablets or dry capsules, as desired, with equivalent results. The composition of the present invention can be compressed at a high rate of compression in a rotary tableting machine as well as a low rate of compression utilizing a single tablet hydraulic unit with effective results.

The product of the invention can also be used as a filler in capsules or as an absorbent for oily material such as fragrances. The product of the invention is anhydrous dicalcium phosphate and can be used as such as is known in the art.

The invention is illustrated in the Examples which follow. All percentages and ratios are by weight unless otherwise stated.

EXAMPLE 1

Dicalcium phosphate dihydrate having a particle size of 95 percent below 44 microns was heated in a continuous rotary turbo tray drier for 2.5 hours at 180° C. until the L.O.I. at 800° C. was reduced from about 25 percent to between about 6.6 and 8.5 percent.

The thus formed anhydrous dicalcium phosphate was granulated and dried in a Glatt TM Powder Coater Granulator model GPCG 5. Comparable samples using precipitated anhydrous dicalcium phosphate were also prepared. The formulations, granulation conditions, drying conditions and results are set forth in the following table. The inlet air set-point during granulation was 60° C. and during drying 70° C. Unmodified U.S.P. corn starch (National's Purity 21 TM) was used as a binder in Experiments 1-8. Sieving is based on U.S. Standard Sieve Series.

As used in this Example DCPA means anhydrous dicalcium phosphate.

Soft is intended to mean a dentin abrasion value of less than about 100.

Regular is intended to mean a dentin abrasion value of greater than about 100.

Actual dentin abrasion values were not run on some or all of the samples in these Examples. The differentiation of soft and regular is based on an extrapolation of dentin abrasion values actually obtained on similar dicalcium phosphate dihydrate samples.

TABLE I

| Experiment | 1 | 2 | 3 | 4 | 5 | 6 | 7 | 8 |
|---|---|---|---|---|---|---|---|---|
| FORMULATION: | | | | | | | | |
| DCPA, g | 8000 | 8000 | 8000 | 8000 | 12000 | 12000 | 12000 | 8000 |
| DCPA, type | Soft | Soft | Soft | Soft | Regular | Regular | Regular | Regular |
| Starch, g | 400(5%) | 400(5%) | 240(3%) | 240(3%) | 360(3%) | 360(3%) | 600(5%) | 400(5%) |
| Water, g | 6300 | 6300 | 3760 | 3760 | 5640 | 5640 | 9400 | 6300 |
| FLUIDIZATION AIR: | | | | | | | | |
| Air Volume, m3/h | 200-400 | 200-400 | 200-400 | 200-400 | 200-400 | 200-400 | 200-500 | 200-500 |
| Dry Bulb, C | 22.0 | 20.5 | 21.0 | 21.0 | 9.5 | 9.6 | 7.0 | 20.5 |
| Wet Bulb, C | 15.0 | 16.0 | 15.1 | 15.0 | 18.0 | 18.6 | 13.5 | 16.0 |
| BINDER ATOMIZATION: | | | | | | | | |
| Spray Rate, ml/min | 200-400 | 200-400 | 225 | 200-400 | 225 | 225 | 225 | 200-500 |
| Atom. Pressure, bar | 3 | 3 | 3 | 3 | 3 | 3 | 2.5 | 3 |
| Atom. Air Rate, m3/h | 18 | 18 | 18 | 18 | 16.8 | 16.8 | 14.8 | 18 |
| Nozzle Diameter, mm | 2.2 | 2.2 | 2.2 | 2.2 | 2.2 | 2.2 | 2.2 | 2.2 |
| BATCH CYCLE: | | | | | | | | |
| Spraying Stage, min | 22 | 42 | 19 | 12 | 33 | 30 | 48 | 32 |
| Drying Stage, min | 44 | 33 | 24 | 32 | 14 | 19 | 33 | 16 |
| PRODUCT DENSITY: | | | | | | | | |
| Loose Bulk, g/cc | .64 | .60 | .62 | .65 | .81 | .87 | .86 | .83 |
| Tapped 50 times, g/cc | .71 | .67 | .73 | .72 | .92 | .95 | .96 | .91 |
| PRODUCT SIEVING: | | | | | | | | |
| Wt. % on 40 mesh | 13 | 1 | Trace | 1 | 1 | 2 | 22 | 37 |
| 60 mesh | 36 | 18 | 2 | 10 | 9 | 15 | 55 | 55 |
| 100 mesh | 27 | 39 | 15 | 18 | 38 | 39 | 21 | 8 |
| 200 mesh | 16 | 30 | 30 | 24 | 46 | 37 | 1 | Trace |
| 325 mesh | 4 | 7 | 52 | 46 | 6 | 5 | Trace | Trace |
| −325 mesh | 3 | 6 | — | — | 1 | 2 | Trace | Trace |

Soft dicalcium phosphate anhydrous produced an excellent product when granulated with 5 percent starch as is shown in Experiments 1 and 2. About 87 percent of the product of Experiment 2 fell between about 40 and about 200 mesh. The product had excellent flow properties. Increase in the binder spray rate over that used in Experiment 3 improved the product (Experiment 4).

Experiments 5 and 6 used 5 percent starch in granulating precipitated anhydrous dicalcium phosphate which resulted in coarse products. Experiments 7 and 8 used 3 percent starch to granulate precipitated anhydrous dicalcium phosphate. A product with a particle size desirable for direct compression tableting was obtained.

In theory, the soft anhydrous dicalcium phosphate has more surface area which may require an increase in binder amount to reach the degree of granulation required for tableting. Optimum levels of binder can be achieved without undue experimentation.

EXAMPLE 2

The procedure of Example 1 was repeated using acacia powder, USP-NF grade, as the binder.
The following results were obtained:

TABLE II

| Experiment | 9 | 10 | 11 | 12 |
|---|---|---|---|---|
| FORMULATION: | | | | |
| DCPA, g | 8000 | 8000 | 8000 | 8000 |
| DCPA, type | Soft | Soft | Regular | Regular |
| Acacia, g | 400(5%) | 400(5%) | 400(5%) | 400(5%) |
| Water, g | 5000 | 6000 | 4000 | 4000 |
| FLUIDIZATION AIR: | | | | |
| Air Volume, m3/h | 100–500 | 400–500 | 400–500 | 100–400 |
| Dry Bulb, C | 25.0 | 19.5 | 19.5 | 25.0 |
| Wet Bulb, C | 15.5 | 16.0 | 16.0 | 15.5 |
| BINDER ATOMIZATION: | | | | |
| Spray Rate, ml/min | 150–275 | 200–400 | 200 | 130–200 |
| Atom. Pressure, bar | 2 | 3 | 3 | 2.5 |
| Atom. Air Rate, m3/h | 12.7 | 18 | 18 | 15 |
| Nozzle Diameter, mm | 1.2 | 1.2 | 1.2 | 1.2 |
| BATCH CYCLE: | | | | |
| Spraying Stage, min | 29 | 20 | 22 | 31 |
| Drying Stage, min | 18 | 20 | 22 | 17 |
| PRODUCT DENSITY: | | | | |
| Loose Bulk, g/cc | — | — | .90 | .89 |
| Tapped 50 times, g/cc | — | — | 1.00 | .93 |
| PRODUCT SIEVING: | | | | |
| Wt. % on 40 mesh | 0 | | 6 | 1 |
| 60 mesh | 1 | RUN WAS | 9 | 2 |
| 100 mesh | 3 | ABORTED | 9 | 5 |
| 200 mesh | 4 | DUE TO | 38 | 60 |
| 325 mesh | 5 | OVERWETTING | 38 | 30 |
| −325 mesh | 87 | | — | 2 |

Acacia gum appeared to be a weaker binder than starch. Larger amounts of acacia appear necessary to obtain satisfactory results. Binder level can be optimized without undue experimentation.

In Examples 3–5 the experiment numbers refer to Examples 1 and 2.

EXAMPLE 3

Surface Area

The surface area of the granulated products of some of the Experiments was determined and compared to the surface area of the starting materials. Surface area was determined by the BET nitrogen absorption method. The results are reported in Table III.

TABLE III
SUMMARY OF SURFACE AREA ANALYSIS

| Experiment | Formulation | Surface Area (BET) meters$^2$/g |
|---|---|---|
| Ungranulated Controls | Precipitated DCPA Powder | 1.8 |
| | Soft DCPA Powder | 13.6 |
| 1 | Soft DCPA + 5% Starch | 9.9 |
| 5 | Precipitated DCPA + 3% Starch | 1.3 |
| 7 | Precipitated DCPA + 5% Starch | 1.3 |
| 9 | Soft DCPA + 5% Acacia | 7.7 |
| 12 | Precipitated DCPA + 5% Acacia | .8 |

As can be seen from this data, the original soft anhydrous dicalcium phosphate has a surface area more than 7.5 times larger than precipitated anhydrous dicalcium phosphate. After granulation with starch, the surface area in both products has been reduced by about 27 percent. More surface area is lost in granulating with acacia at the percentage used. In theory, the binder solution containing the acacia is less viscous than the starch binder solution allowing more binder to be absorbed by the porous particles thus reducing surface area.

EXAMPLE 4

Flowability

The flowability of the granulated product was tested by determining the time needed to empty funnels of various orifice sizes and varying volumes filled to the top and leveled. The numbers given in parentheses are volumes based on milliliters. Controls were a dicalcium phosphate dihydrate, unmilled, sold under the trademark DI-TAB® and tricalcium phosphate sold under the trademark TRI-TAB®.

TABLE IV
FLOWABILITY OF GRANULATED DCPA

| | | Time (seconds) to empty funnels with orifice of: | | | | |
|---|---|---|---|---|---|---|
| Ex. | Formulation | 2.5 mm (75 ml) | 5.0 mm (72 ml) | 8.0 mm (82 ml) | 12.0 mm (84 ml) | 18.0 mm (84 ml) |
| 1 | Soft DCPA + 5% Starch | 205 | 18.7 | 5.8 | 3.5 | .9 |
| 2 | Soft DCPA + 5% Starch | 196 | 21.1 | 6.7 | 4.4 | 1.1 |
| 5 | Prec. DCPA + 3% Starch | 174 | 19.3 | 6.7 | 4.1 | 1.0 |
| 6 | Prec. DCPA + 3% Starch | 180 | 18.7 | 6.6 | 4.0 | .9 |
| 7 | Prec. DCPA + 5% Starch | Failed | 18.1 | 5.8 | 3.2 | .9 |
| 8 | Prec. DCPA + 5% Starch | Failed | 20.5 | 5.9 | 3.2 | .8 |
| 9 | Soft DCPA + 5% Acacia | N/T | N/T | N/T | N/T | Failed |
| 12 | Prec. DCPA + 5% Acacia | 172 | 26.0 | 8.5 | 5.0 | 1.4 |
| Control Samples: | | | | | | |
| DI-TAB ® DCPD | | 177 | 18.2 | 6.0 | 3.4 | 1.0 |
| TRI-TAB ® TCP | | Failed | 30.0 | 9.4 | 5.5 | N/T |

N/T means Not Tested

EXAMPLE 5

Tableting

Seven hundred fifty milligrams of each blend was blended for 2 minutes with 0.5 percent magnesium stearate lubricant and compressed separately in a ½ inch flat-faced punch and die system using a hydraulic press (Fred Carver, Inc. Model C-12). Tablet hardness was determined using a Schleuniger Tablet Hardness Tester, Model 2E/106. Tablet hardness (average of 3) is given in the following table in terms of applied force.

Tablet thickness is an average height of 3 tablets. Compressed density is determined by dividing the weight of the tablet by the volume. The reported value is the average of 3 tablets.

TABLE V
TABLET HARDNESS, KILOPONDS

| | DCPA | | Tablet Hardness, Kiloponds | | | |
|---|---|---|---|---|---|---|
| Ex. | Type | % | 0.5 MT | 1 MT | 2 MT | 3 MT* |
| 1 | Soft | 5 | 7.2 | 15.2 | NB >20 | NB >20 |
| 2 | Soft | 5 | 8.4 | 14.1 | NB >20 | NB >20 |
| 5 | Precip. | 3 | 3.0 | 6.1 | 12.2 | 19.1 |
| 6 | Precip. | 3 | 3.9 | 7.0 | 13.1 | 18.5 |
| 7 | Precip. | 5 | 5.2 | 8.1 | 14.6 | B >20 |
| 8 | Precip. | 5 | 4.9 | 8.6 | 15.2 | B >20 |
| 9 | Soft | 5 | 4.0 | 8.2 | 15.6 | NB >20 |
| 12 | Precip. | 5 | 2.4 | 4.6 | 11.5 | 15.8 |

*B means broken at machine limits of 20 kiloponds
NB means not broken at machine limits of 20 kiloponds

TABLE VI
TABLET THICKNESS, MILLIMETERS

| | | Tablet Thickness, mm | | | |
|---|---|---|---|---|---|
| Ex. | Formulation | 0.5 MT | 1 MT | 2 MT | 3 MT |
| 1 | Soft DCPA + 5% Starch | 4.125 | 3.814 | 3.431 | 3.215 |
| 2 | Soft DCPA + 5% Starch | 4.228 | 3.840 | 3.363 | 3.181 |
| 8 | Prec. DCPA + 5% Starch | 3.508 | 3.209 | 3.008 | 2.857 |
| 9 | Soft DCPA + 5% Acacia | 3.905 | 3.634 | 3.325 | 3.152 |
| 12 | Prec. DCPA + 5% Acacia | 3.609 | 3.298 | 2.945 | 2.791 |

TABLE VII
TABLET COMPRESSED DENSITY, GRAMS/CUBIC CENTIMETER

| | | Compressed Density, g/cc | | | |
|---|---|---|---|---|---|
| Ex. | Formulation | 0.5 MT | 1 MT | 2 MT | 3 MT |
| 1 | Soft DCPA + 5% Starch | 1.44 | 1.55 | 1.73 | 1.84 |
| 2 | Soft DCPA + 5% Starch | 1.40 | 1.54 | 1.76 | 1.861 |
| 8 | Prec. DCPA + 5% Starch | 1.69 | 1.84 | 1.97 | 2.07 |
| 9 | Soft DCPA + 5% Acacia | 1.52 | 1.63 | 1.78 | 1.88 |
| 12 | Prec. DCPA + 5% Acacia | 1.64 | 1.80 | 2.01 | 2.12 |

EXAMPLE 6

Effect of Microcrystalline Cellulose on Compressibility

Tablets were prepared using the formulations set forth in Table VIII by mixing the anhydrous dicalcium phosphate with the microcrystalline cellulose in a twin shell V-blender (Patterson-Kelley). The soft DCPa was the granulated product of Experiment 1. The precipitated DCPA used was the granulated product of Experiment 5. After mixing for 20 minutes, 0.5 percent magnesium stearate as lubricant was added and the mixture was blended an additional 2 minutes. Tablets were prepared and tested for hardness as outlined hereinbelow. The results are reported in Table VIII as follows:

TABLE VIII
EFFECT OF MICROCRYSTALLINE CELLULOSE ON THE COMPRESSIBILITY OF DCPA

| Type of DCPA | % of DCPA | % of Microcrystalline Cellulose* | Tablet Hardness, kiloponds | | | |
|---|---|---|---|---|---|---|
| | | | 0.5 MT | 1 MT | 2 MT | 3 MT |
| Soft | 100 | 0 | 7.2 | 15.2 | >20 | >20 |
| Precip. | 100 | 0 | 3.0 | 6.1 | 12.2 | 19.1 |
| Precip. | 90 | 10 | 5.0 | 9.0 | 15.5 | >20 |
| Precip. | 80 | 20 | 7.6 | 13.3 | >20 | >20 |

*Avicel ® PH 101 microcrystalline cellulose from FMC Corp.

As can be seen from the data, the granulated soft DCPA of the invention without the expensive microcrystalline cellulose tablet hardening agent unexpectedly provides tablets as hard or harder than precipitated DCPA with 20 percent added microcrystalline cellulose. This effect was obtained without a reduction in disintegration properties. The product of the invention achieves adequate hardness without the need for hardening agents.

What is claimed is:

1. A process for preparing a directly compressible soft anhydrous dicalcium phosphate which comprises dehydrating dicalcium phosphate dihydrate of a particle size insufficient for effective direct compression tableting in an amount sufficient to form anhydrous dicalcium phosphate having a Loss on Ignition of about 11 percent by weight or less, said anhydrous particles having a surface area greater than 5 meters$^2$/gram and granulating with a binder the particles of anhydrous dicalcium phosphate so formed wherein at least 90 percent of the granules of anhydrous dicalcium phosphate are greater than 44 microns, said granular anhydrous dicalcium phosphate having a Radioactivity Dentin Abrasivity of below about 150.

2. The process as recited in claim 1 wherein the particle size of at least 10 percent of said dicalcium phosphate is below 44 microns.

3. The process of claim 1 wherein at least 80 percent of the granules of anhydrous dicalcium phosphate are greater than 74 microns.

4. The process according to claim 1 wherein the particle size of the granules of anhydrous dicalcium phosphate range from about 44 to about 840 microns.

5. The process as recited in claim 1 wherein the particles are dehydrated sufficient to reduce the Loss on Ignition to an amount within the range of from about 8.5 percent to about 6.6 percent by weight.

6. The process as recited in claim 1 wherein said binder is selected from the group consisting of starches, gums, synthetic polymers, cellulose derivatives, and gelatins.

7. The process as recited in claim 1 wherein the binder is acacia gum.

8. The process as recited in claim 1 wherein said binder is starch.

9. The product of the process of claim 1.

10. The product of the process of claim 6.

11. A process for preparing tablets or dry capsules by direct compression which comprises directly compressing the product of claim 9 into a tablet form.

12. A process for preparing tablets or dry capsules by direct compression which comprises directly compressing the product of claim 10 into a tablet form.

* * * * *

UNITED STATES PATENT AND TRADEMARK OFFICE
CERTIFICATE OF CORRECTION

PATENT NO. : 4,675,188
DATED : June 23, 1987
INVENTOR(S) : Chihang R. Chu

It is certified that error appears in the above—identified patent and that said Letters Patent is hereby corrected as shown below:

Col. 1, line 14 - "employes" should be -- employs --;

Col. 1, line 20 - "compression" should be -- compressible --;

Col. 1, line 51 - "be" should be -- been --;

Col. 6, line 10 - "drier" should be -- dryer --;

Col. 6, Table I - Experiments 5-7, under title "Fluidization Air" subtitle Dry Bulb, the numbers "9.5  9.6  7.0" should be -- 18.0  18.6  13.5 --'

Col. 6, Table I - Experiments 5-7, under title "Fluidization Air" subtitle Wet Bulb, the numbers "18.0  18.6  13.5" should be -- 9.5  9.6  7.0 --;

Col. 10, line 35 - "DCPa" should be -- DCPA --;

Col. 10, line 41 - "hereinbelow" should be -- hereinbefore --;

Col. 7, line 3 - the numbers "5 and 6" should be -- 7 and 8 --;

Col. 7, line 5 - the numbers "7 and 8" should be -- 5 and 6 --.

Signed and Sealed this

Twenty-ninth Day of December, 1987

Attest:

DONALD J. QUIGG

Attesting Officer

Commissioner of Patents and Trademarks